(12) United States Patent
Lee et al.

(10) Patent No.: US 10,421,781 B2
(45) Date of Patent: Sep. 24, 2019

(54) ANTIMICROBIAL PEPTIDE AND USE THEREOF

(71) Applicant: NOVACELL TECHNOLOGY INC., Gyeongsangbuk-do (KR)

(72) Inventors: Tae Hoon Lee, Seoul (KR); Jae Yoon Kim, Gyeongsangbuk-do (KR); Jae Wang Ghim, Gyeongsangbuk-do (KR); Sun Ho Kee, Seoul (KR)

(73) Assignee: NOVACELL TECHNOLOGY INC., Gyeongsangbuk-Do (KR)

( * ) Notice: Subject to any disclaimer, the term of this patent is extended or adjusted under 35 U.S.C. 154(b) by 0 days.

(21) Appl. No.: 15/775,085

(22) PCT Filed: Oct. 5, 2016

(86) PCT No.: PCT/KR2016/011135
§ 371 (c)(1),
(2) Date: May 10, 2018

(87) PCT Pub. No.: WO2017/086596
PCT Pub. Date: May 26, 2017

(65) Prior Publication Data
US 2018/0319840 A1 Nov. 8, 2018

(30) Foreign Application Priority Data

Nov. 18, 2015 (KR) .................. 10-2015-0161837

(51) Int. Cl.
| | | |
|---|---|---|
| *A61K 38/00* | (2006.01) |
| *A61K 38/08* | (2019.01) |
| *A61K 8/64* | (2006.01) |
| *A61P 17/00* | (2006.01) |
| *A61Q 19/00* | (2006.01) |
| *C07K 7/06* | (2006.01) |
| *C07K 7/00* | (2006.01) |

(52) U.S. Cl.
CPC ............... *C07K 7/06* (2013.01); *A61K 8/64* (2013.01); *A61K 38/08* (2013.01); *A61P 17/00* (2018.01); *A61Q 19/00* (2013.01); *A61K 38/00* (2013.01); *Y02A 50/473* (2018.01)

(58) Field of Classification Search
CPC .......... A61K 38/00; A61K 38/08; A61K 8/64; C07K 7/06; C07K 7/00; A61Q 19/00; A61P 17/00
USPC ................. 514/2.4, 21.7, 18.8; 530/329, 300
See application file for complete search history.

(56) References Cited

U.S. PATENT DOCUMENTS

| 5,470,950 A | 11/1995 | Maloy et al. |
| 8,633,164 B2 * | 1/2014 | Brandenburg ... C07K 14/43509 435/252.3 |
| 2009/0233870 A1 | 9/2009 | Blondelle et al. |
| 2011/0105416 A1 | 5/2011 | Brandenburg |
| 2015/0080291 A1 | 3/2015 | Zhang et al. |

FOREIGN PATENT DOCUMENTS

KR  1020110137238 A  12/2011

OTHER PUBLICATIONS

A0A0A9CG20_ARUDO from UniProt, pp. 1-3. Iintegrated into UniProtKB/TrEMBL Mar. 4, 2015.*
Duru, et al. "Role of Formic Receptors in Soluble Urokinase Receptor Induced Human Vascular Smooth Muscle Migration" J Surg Res. May 15, 2015; 195(2): 396-405.
Nakashima et al., "Tricyclic Antidepressant Amitriptyline-induced Glial Cell Linederived Neurotrophic Factor Production Involves Pertussis Toxin-sensitive Gai/o Activation in Astroglial Cells" The Journal of Biological Chemistry vol. 290, No. 22, pp. 13678-13691, May 29, 2015.
Mangmool et al., "Gi/o Protein-Dependent and -Independent Actions of Pertussis Toxin (PTX)" Toxins 2011, 3, 884-899.

* cited by examiner

*Primary Examiner* — Julie Ha
(74) *Attorney, Agent, or Firm* — Mayer & Williams, PC; Stuart H. Mayer

(57) ABSTRACT

A novel peptide has both an antimicrobial effect and an immunocyte activity regulatory function. The peptide regulates immunocyte activity and also exhibits antimicrobial activity against various bacteria such as gram-negative bacteria and gram-positive bacteria, thereby being useful for treating various immune diseases such as atopic dermatitis and for treating diseases caused by the infection of pathogenic bacteria.

16 Claims, 6 Drawing Sheets
Specification includes a Sequence Listing.

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: artificial antimicrobial peptide
<220> FEATURE:
<221> NAME/KEY: VARIANT
<222> LOCATION: (7)
<223> OTHER INFORMATION: D-methionine

<400> SEQUENCE: 1

Lys Phe Lys Trp Arg Tyr Xaa
1               5
```

ANTIMICROBIAL PEPTIDE AND USE THEREOF

TECHNICAL FIELD

The present invention relates to a novel antimicrobial peptide and a use thereof, and more specifically, to a novel peptide having both an antimicrobial effect and a function of regulating immunocyte activity and a use thereof.

BACKGROUND ART

Antimicrobial peptides may be found in nature and may also be found in synthetic peptides. These antimicrobial peptides consist of relatively short amino acid sequences (10 to 100 amino acid residues) compared to normal proteins. When these antimicrobial peptides mostly bind to the cell membrane, 1) they form ion channels on the cell membrane and thereby inhibit the energy production of the microorganism, or 2) generate large holes in the cell membrane, resulting in the death of the cell. Since these antimicrobial peptides physically destroy microorganisms, it is very difficult for microorganisms to have resistance to these antimicrobial peptides unlike conventional antibiotics that inhibit the synthesis of microbial cell walls or intracellular polymers, and thus no resistance to these antimicrobial peptides has been reported until now. Although there is little sequence similarity between many antimicrobial peptides known to date, there appear to be some general tendencies with regard to their structures and activities. Representatively, antimicrobial peptides have a positively-charged moiety, such as lysine, arginine, and histidine, and a hydrophobic moiety. Currently, in the Shai-Matsuzaki-Huang (SMH) model, which appears to be most persuasive among the hypotheses suggested being related to the action mechanism of antimicrobial peptides, the characteristics of sequences and the mechanisms of antimicrobial peptides are described as follows: after the positively-charged hydrophilic moiety binds to the negatively-charged cell membrane of bacteria, the hydrophobic moiety of the peptide bound to the cell membrane interacts with the hydrophobic moiety of the phospholipid of the cell membrane and forms pores on the cell membrane to change the permeability of the cell membrane, thereby destroying the cells. Formyl peptide receptor group (formyl peptide receptor 1 (FPR1) and formyl peptide receptor 2 (FPR2)) expressed in phagocytic cells, such as neutrophils and monocytes, plays an important role in host defense against pathogen infection (Mangmool, S. et al., *Toxins*, 3: 884-899, 2011). These receptors are known to bind to the pertussis toxin-sensitive Gi protein (Nakashima, K. et al., *J. Biol. Chem.*, 290(22): 13678-91, 2015). Between the receptors, FPR2 is known to play an important role in inflammatory diseases. Activation of FPR2 induces the separation of the Gβγ subunit from the Gαi subunit and the βγ-subunit induces the activation of phospholipase Cβ or phosphoinositide 3-kinase (Duru, E. A. et al., *J. Surg. Res.*, 195(2): 396-405, 2015). Activation of these molecules induces complex downstream signaling thereby modulating in vivo immune responses by diversifying cellular responses such as chemotactic migration, degranulation, and superoxide generation.

DISCLOSURE OF THE INVENTION

Technical Problem

The present invention has been made to solve various problems including the problems described above, and thus an objective of the present invention is to provide a novel peptide having both a more efficient antibacterial activity and immunological activity at the same time.

Additionally, another objective of the present invention is to provide various uses of the peptide including an antibacterial agent containing the peptide, a pharmaceutical composition for treating atopic dermatitis, a cosmetic composition for ameliorating atopic skin, etc.

However, these objectives are provided for illustrative purposes and they should not limit the scope of the present invention.

Technical Solution

According to another aspect of the present invention, there is provided a novel antibacterial and immune regulatory peptide consisting of the amino acid sequence of SEQ ID NO: 1.

According to still another aspect of the present invention, there is provided an antibacterial agent containing the peptide as an active ingredient.

According to still another aspect of the present invention, there is provided a pharmaceutical composition for treating atopic dermatitis containing the peptide as an active ingredient.

According to still another aspect of the present invention, there is provided a cosmetic composition for treating atopic dermatitis containing the peptide as an active ingredient.

Advantageous Effects

The antibacterial peptide according to an embodiment of the present invention not only has an extremely high antimicrobial activity against various bacteria such as gram-negative bacteria and gram-positive bacteria but also has an effect for treating atopic dermatitis, and thus, can be used for various purposes such as a skin external agent or cosmetic composition for ameliorating atopic dermatitis as well as an antibiotic.

BRIEF DESCRIPTION OF THE DRAWINGS

FIGS. 2A and 2B show graphs illustrating the FPR2-dependent activity of increasing intracellular calcium ions in immune cells of the peptide having the amino acid sequence of SEQ ID NO: 1 according to an embodiment of the present invention, in which FIG. 2A shows graphs representing the FL ratio of the peptide in RBL cells and RBL cells where FPR2 and FPR1 were overexpressed, respectively; and FIG. 2B shows a graph representing the activity of increasing calcium ions according to the concentration of the peptide of SEQ ID NO: 1 in RBL cells where FPR2 was overexpressed.

FIGS. 4A and 4B show the results confirming the effect of the peptide treatment in ameliorating dermatitis in the dermis and the applied site in the dermis of a model of atopic dermatitis induced by capsaicin, according to an embodiment of the present invention, in which FIG. 4A shows graphs illustrating the effect of ameliorating dermatitis in rats (Neo-Cap) of atopic dermatitis induced by capsaicin treatment, and FIG. 4B shows graphs illustrating the effect of ameliorating dermatitis in 2-week-old rats (2 W Caps) of atopic dermatitis induced by capsaicin treatment.

MODE FOR CARRYING OUT THE INVENTION

Definition of Terms

Figure 1:
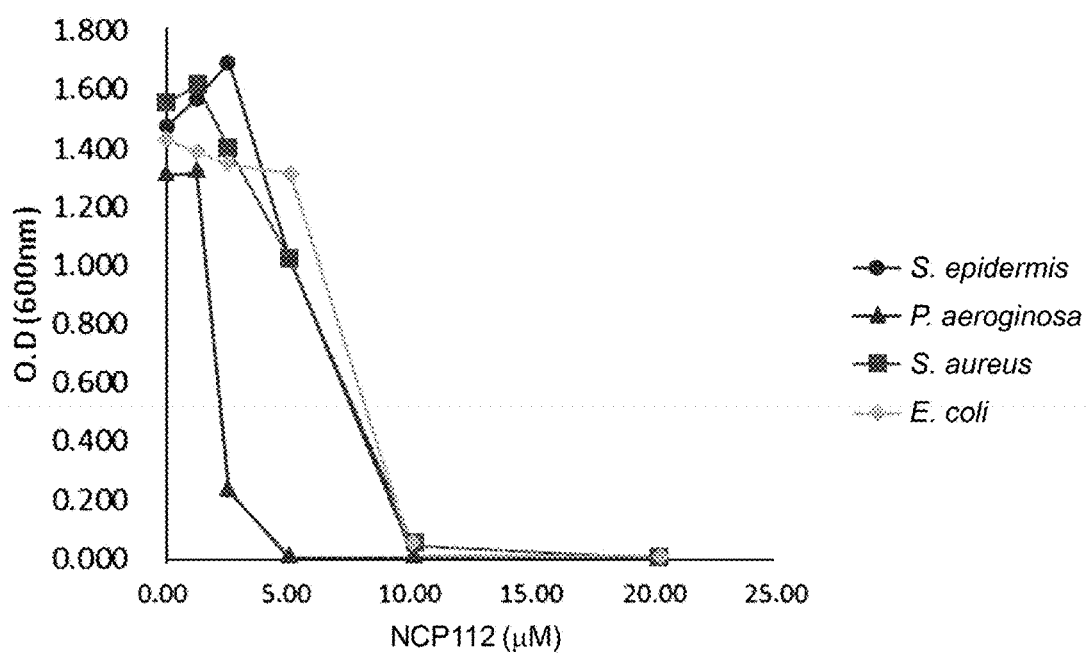
FIG. 1 shows a graph illustrating the results of antibacterial activity of a peptide, which has the amino acid sequence of SEQ ID NO: 1 according to an embodiment of the present invention and in which an octanoyl group is added to the N-terminus, against gram-positive bacteria (*Staphylococcus epidermidis* and *Staphylococcus aureus*) and gram-negative bacteria (*Pseudomonas aeruginosa* and *Escherichia coli*).

The terms as used herein are defined as follows.

As used herein, the term "immune regulatory peptide" refers to a peptide which, while having a non-immunoglobulin protein form, is directly or indirectly involved in immune-strengthening actions such as antibacterial and antiviral activities, inflammatory responses, stimulation of natural killer cells, regulation of antibody-dependent cellular cytotoxicity, etc. In other words, with regard to the protein decoded by the gene, the formyl peptide receptor group (formyl peptide receptor 1 (FPR1) and formyl peptide receptor 2 (FPR2)) expressed in phagocytic cells such as neutrophils and monocytes plays an important role in host defense against pathogen infection. The receptors are known to bind to the pertussis toxin-sensitive Gi protein. Among them, FPR2 is known to play an important role in inflammatory diseases. Activation of FPR1 and FPR2 induces the separation of the G$\beta\gamma$ subunit from the G$\alpha$i subunit and the $\beta\gamma$-subunit induces the activation of phospholipase C$\beta$, or phosphoinositide 3-kinase. Activation of these molecules induces complex downstream signaling thereby diversifying cellular responses such as chemotactic migration, degranulation, and superoxide generation.

As used herein, the term "antimicrobial peptide" refers to a cationic peptide compound which is generally composed of a relatively simple structure having a broad antimicrobial spectrum with regard to gram-positive bacteria, gram-negative bacteria, fungi, viruses, etc. Although the mechanism of antimicrobial peptides is not yet fully understood, they are generally known to exhibit antibacterial activity through an action mechanism that destroys cell membranes of microorganisms.

As used herein, the term "atopic dermatitis" refers to the most common inflammatory skin disease in infants and children and it is characterized by severe pruritus, erythema, edema, exudation, scab, scale, lichenification, etc. Atopic dermatitis relapses frequently, progresses chronically, and exhibits characteristic secondary lesions such as scratches, lichenifications, etc., due to repeated scratching of the skin.

DETAILED DESCRIPTION OF THE INVENTION

Hereinafter, the present invention will be described in detail.

According to an aspect of the present invention, there is provided a novel antibacterial and immune regulatory peptide consisting of the amino acid sequence of SEQ ID NO: 1.

The peptide may be one in which an octanoyl group ($CH_3(CH_2)_6CO$—, hereinafter abbreviated as 'Oct-') is attached, or may be one in which one to six amino acids are attached to the C-terminus of the peptide. According to another aspect of the present invention, there is provided an antibacterial agent which contains the peptide as an active ingredient.

The antibacterial agent may have an antibacterial activity against gram-negative bacteria and gram-positive bacteria, in which the gram-negative bacteria may be *E. coli*, *Salmonella* sp., *Vibrio* sp., or *Pseudomonas aeruginosa*, and the gram-positive bacteria may be *Staphylococcus aureus*, *Staphylococcus epidermidis*, *Propionibacterium acnes*, or *Streptomyces mutans*.

According to still another aspect of the present invention, there is provided a pharmaceutical composition for treating atopic dermatitis containing the peptide as an active ingredient.

The pharmaceutical composition containing the peptide as an active ingredient may include at least one pharmaceutical diluent selected from saline, buffered saline, dextrose, water, glycerol, and ethanol, but the diluent is not limited thereto.

The pharmaceutical composition may be applied differently depending on the purpose of administration and diseases. The amount of the active ingredient to be actually administered must be determined in consideration of various factors, that is, the disease to be treated, level of conditions of a patient, presence of administration in combination with a different drug (e.g., a chemotactic drug), age, sex, weight, and diet of a patient, duration of administration, administration route, and administration rate of the composition. Although the dose and administration route of the composition may be adjusted depending on the type and severity of the disease, the composition may be administered once daily or one to three times in divided doses daily.

The composition containing the peptide or material of the invention may be administered orally or parenterally. Parenteral administration refers to an administration of a drug through a route other than oral administration, such as rectal, intravenous, peritoneal and muscular, arterial, transdermal, nasal, inhalation, ocular, and subcutaneous administration. The pharmaceutical composition containing the peptide or material may be formulated in any form, such as an oral dosage form, injectable solution, or topical preparation. The formulation is preferably prepared to be suitable for oral and injectable administrations (true solutions, suspensions, or emulsions) and most preferably, the formulation is prepared in an oral dosage form such as tablets, capsules, soft capsules, aqueous medicaments, pills, granules, etc. In the formulation, the peptide of the present invention is filled into a soft capsule without an excipient, and mixed with the carrier or diluted to be prepared into a suitable preparation. Examples of suitable carriers include starch, water, saline, Ringer's solution, dextrose, etc.

According to still another aspect of the present invention, there is provided a cosmetic composition for ameliorating atopic dermatitis containing the peptide.

The cosmetic composition may contain at least one additive used in the formulation of cosmetic compositions. For example, the additive may include 1,3-butylene glycol, soybean phospholipid choline, sphingosine, cholesterol, Tween80, phytosphingosine, salicylic acid, a skin moisturizer (humectant), a softener, natural oil, keratin, lipoid, a absorbent water-soluble material, stratum corneum ceramide, epidermal lipid acid film fatty acid, cholesteryl ester, ethanol, distilled water, etc.

MODE OF INVENTION

Hereinafter, the present invention will be described in more detail through Examples and Experimental Examples. However, the present invention is not limited to these Examples and Experimental Examples described below, but may be implemented in various other forms, and the following Examples and Experimental Examples are provided to complete the disclosure of the present invention and to fully disclose the scope of the invention to those skilled in the art.

Example 1: Preparation of Antimicrobial Peptides

The present inventors have screened for peptides composed of the amino acid sequence (KFKWRYm) described by SEQ ID NO: 1 with antimicrobial activity by basic screening. In the amino acid sequence of the peptide, each of the upper case letters indicates a normal L-type amino acid and the lower case letter 'm' indicates a D-type methionine. The peptide can be prepared using a conventional method for amino acid synthesis (Umbarger, H. E., *Ann. Rev. Biochem.*, 47: 533-606, 1978).

Example 2: Modification of Antimicrobial Peptides

In order to further improve the antibacterial activity of the peptides that underwent the basic screening in Example 1, the present inventors have examined the antibacterial activity of these peptides by synthesizing modified peptides in which various lipid components, such as a palmitoyl group, an octanoyl group, etc., were attached to the N-terminus of these peptides. As a result, it was confirmed that the modified peptide in which an octanoyl group was attached has the highest activity, and thus, the Oct-KFKWRYm peptide (hereinafter, assigned as 'NCP112') was used in the subsequent experiments.

Example 1: Experiment on Antibacterial Activity of Novel Peptide

In order to further improve the antibacterial activity of the peptides prepared in Example 2, an antibacterial test was performed. Gram-positive bacteria *Staphylococcus epidermidis* and *Staphylococcus aureus*) and gram-negative bacteria (*Pseudomonas aeruginosa* and *E. coli*) were prepared, streaked on agar plate medium using a four-quadrant sequential streak technique, and cultured in a 36° C. incubator overnight. On the next day, the strain colonies on the agar plate medium were inoculated into nutrient broth (3 mL) and cultured overnight at 36° C. and 220 rpm in a shaking incubator. On the next day, the bacteria culture was diluted and the absorbance at 600 nm was measured and adjusted to 0.5. Then, the bacteria culture was diluted in nutrient broth in a 1:100 ratio. Then, the peptides prepared in Example 2 were sequentially diluted in nutrient broth at concentrations of 0 μM, 1.25 μM, 2.5 μM, 5 μM, 10 μM, and 20 μM in an amount of 1 mL, respectively, and 1 mL of the diluted bacteria was inoculated, and cultured overnight at 36° C. and 220 rpm in a shaking incubator for 18 hours. Then, the absorbance was measured at 600 nm and the results were analyzed.

As a result, as shown in FIG. 1, the peptide according to an embodiment of the present invention exhibited antibacterial activity against all of the bacteria in a concentration-dependent manner. In particular, the peptide completely inhibited the growth of 4 kinds of bacteria at a concentration of 10 μM. Among the 4 kinds of bacteria, *P. aeruginosa* was shown to have the highest antibacterial effect.

Example 2: Analysis of Intracellular Ca Ions Through FPRL1

Figure 2:
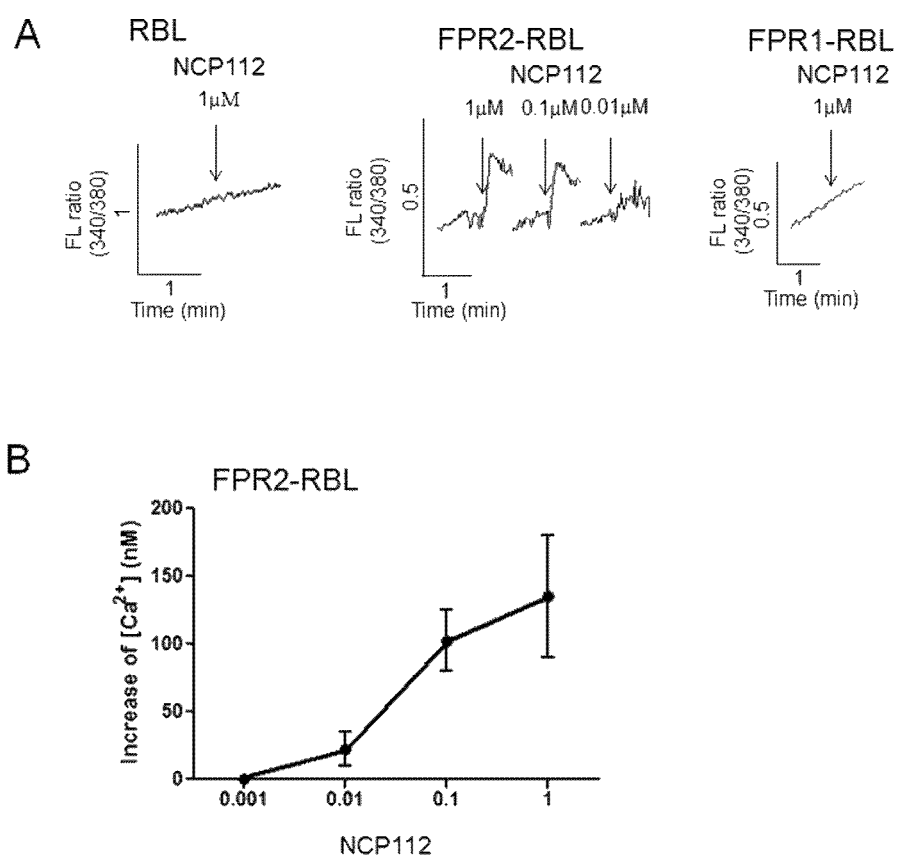

To examine whether the peptide according to an embodiment of the present invention activates the in vivo immunological function of a living organism, the present inventors observed the changes in calcium ion permeability. Specifically, they measured the concentration of intracellular calcium ions to examine whether the peptide activates FPR2. To this end, the present inventors used RBL cells in which FPR2 was not expressed, RBL cells in which FPR1 was overexpressed (FPR1-RBL), and RBL cells in which FPR2 was overexpressed, and used Fura-2/AM, a staining material having a strong binding affinity for calcium, as a method for sensitive measurement of the release of intracellular calcium ions. That is, the cells were cultured in RPMI medium containing 10% fetal bovine serum, centrifuged in the mid-log phase (1 to $3 \times 10^7$ cells/mL), and harvested. Then, the cells were washed several times with RPMI medium containing no fetal bovine serum and resuspended in RPMI medium to a concentration of $1 \times 10^7$ cells/mL. Then, the Fura-2/AM at a final concentration of 3 μM was added thereto and incubated in an incubator (37° C., 5% $CO_2$) for 45 minutes with continuous stirring. After the appropriate time elapsed, the cells were harvested and washed again several times with RPMI medium. Then, the cells were suspended in an appropriate amount of RPMI medium, in which sulfinpyrazone was supplemented at a concentration of 250 μM, so as to prevent the Fura-2 that entered into the cells from being released to the outside of the cells. Approximately $2 \times 10^6$ cells were taken each time and harvested by rapid centrifugation, and resuspended in 1 mL of Locke solution in which EGTA was added but no calcium ions were added, and the absorbance ratios at two wavelengths of 340 nm and 380 nm were monitored on a spectrophotometer. After treating with the peptide of the present invention at different concentrations (1 μM, 0.1 μM, and 0.01 μM) at intervals of about 1 minute, the difference in absorbance at two wavelengths of 340 nm and 380 nm was examined and this was later converted to the concentration of calcium ions freed into the cells according to the method of Grynkiewicz. As a result, as shown in FIG. 2, when the cells were treated with the peptide according to an embodiment of the present invention, the intracellular calcium ions were rapidly increased specifically in FPR2-RBL cells (A), and the amount of intracellular concentration increase of calcium ions according to the peptide treatment exhibited a concentration-dependent feature (B). This suggests that the peptide according to an embodiment of the present invention can regulate the immunological function of a subject through the binding to FPR2 and activation thereafter.

Experimental Example 3: Effect of Amelioration of Dermatitis in Model of Atopic Dermatitis 3-1: Analysis of External Changes
As such, to confirm whether the peptide according to an embodiment of the present invention can actually treat immune-related diseases by activating immunological functions in vivo, the present inventors examined whether the symptoms of atopic dermatitis can be ameliorated by treating the peptide on the animal model of atopic dermatitis. Specifically, to confirm whether the peptide has the effect of ameliorating dermatitis in a model of atopic dermatitis induced by capsaicin, the present inventors observed the degree of skin improvement after treating the peptide (NCP112) according to an embodiment of the present invention on the animals with atopy (Neo-Cap and 2 W Cap) in the dermis of atopy-induced skin tissue, the applied site in the dermis, and the site with scratches. Neo-Cap, which is a representative model of atopic dermatitis, was subcutaneously injected with capsaicin (50 mg/kg) on the back skin of neonatal rats (Sprague Dawley rats) of less than 48 hours to induce atopic dermatitis. 2 W Cap, which is a model mimicking of atopic dermatitis developed in adolescent period or adults, was subcutaneously injected twice with capsaicin (25 mg/kg) of 2-week-old rats (Sprague Dawley) to induce atopic dermatitis.

Figure 3:
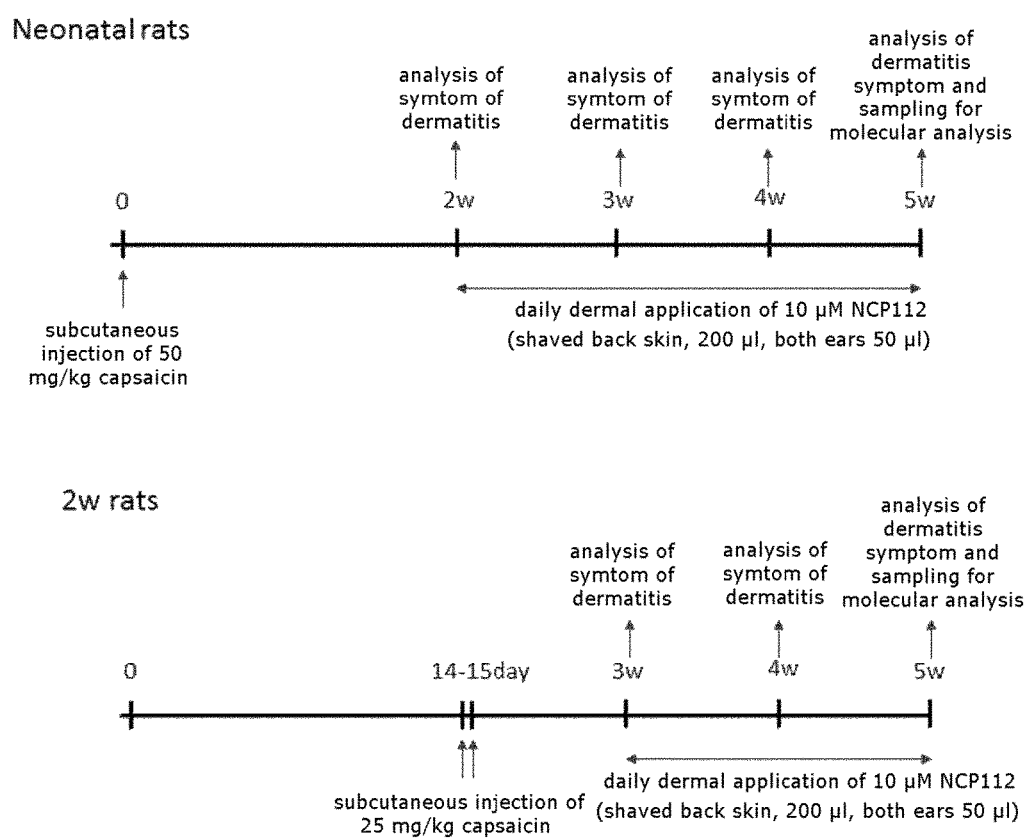
FIG. 3 shows schematic diagrams illustrating the experimental procedure in a model of atopic dermatitis induced by capsaicin at the time of the peptide treatment according to an embodiment of the present invention.
Figure 4:
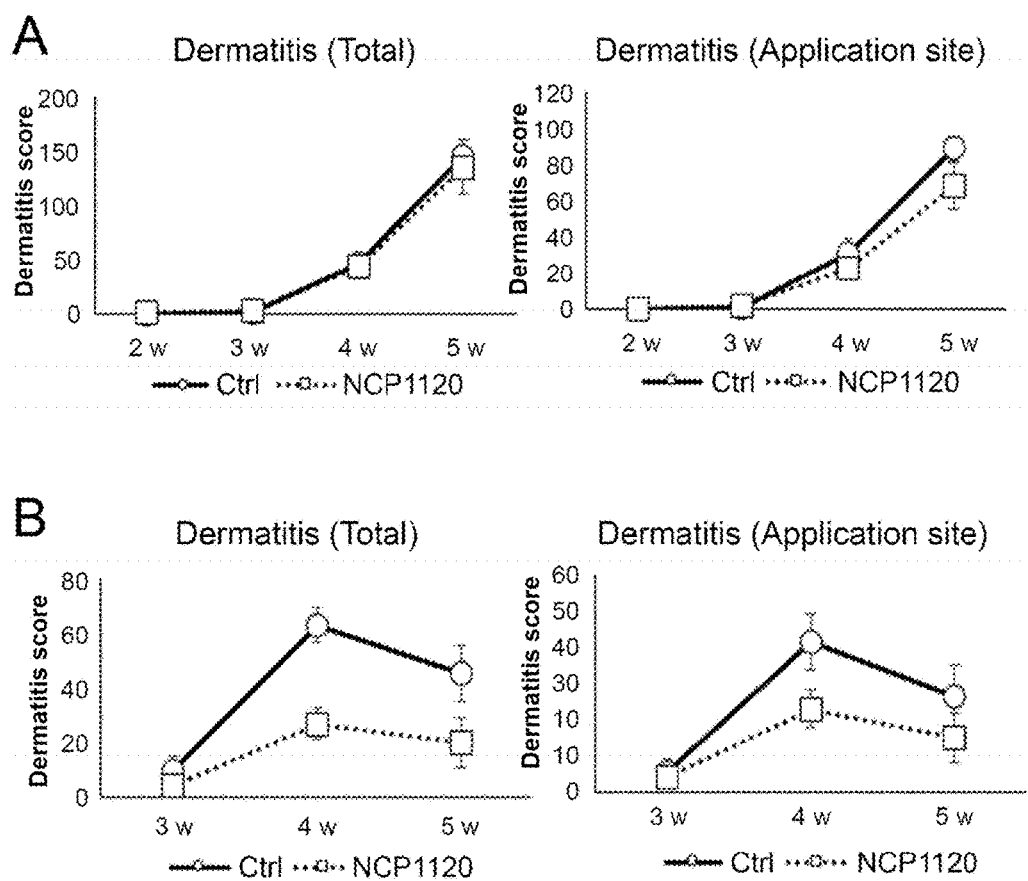

The specific experimental procedure is shown in FIG. 3. In Neo-Cap model, the dermatitis score was measured two weeks after the injection of capsaicin, and the control group (PBS) and NCP112 were applied daily on the back (200 μL) and both ears (50 μL) at a concentration of 10 μM, and the dermatitis score was measured at one-week intervals for three weeks. The dermatitis score was measured on the face, ears, back (total) and ears, and back (application site) according to skin conditions, and the score was standardized by setting the score at the second week (i.e., the starting point) at 1, as shown in FIG. 4. The references are shown in Table 1 below.

TABLE 1

| Position | Score | Skin Conditions |
|---|---|---|
| Face | 0 | Normal |
|  | 1 | Sparse Hair |
|  | 2 | Hair Loss and Erythema |
|  | 3 | Hemorrhage or Ulcer Lesion |
| Ear | 0 | Normal |
|  | 1 | Erythema |
|  | 2 | Hemorrhage |
|  | 3 | Loss of Ear Tissue |
| Back | 0 | Normal |
|  | 1 | Sparse Hair |
|  | 2 | Hair Loss and Erythema |
|  | 3 | Hemorrhage or Ulcer Lesion |

In 2 W-Cap model, the dermatitis score was measured one week after the capsaicin injection, and the control group (PBS) and NCP112 were applied daily on the back (200 μL) and both ears (50 μL) at a concentration of 10 μM, and the dermatitis score was measured at one-week intervals for two weeks, in the same manner as in Neo-Cap model. The score was standardized by setting the score at 3 w (i.e., the starting point) at 1, as shown in FIG. 4.

3-2: Evaluation of Skin Histopathology and Thickness of Atopic Dermatitis

Figure 5:
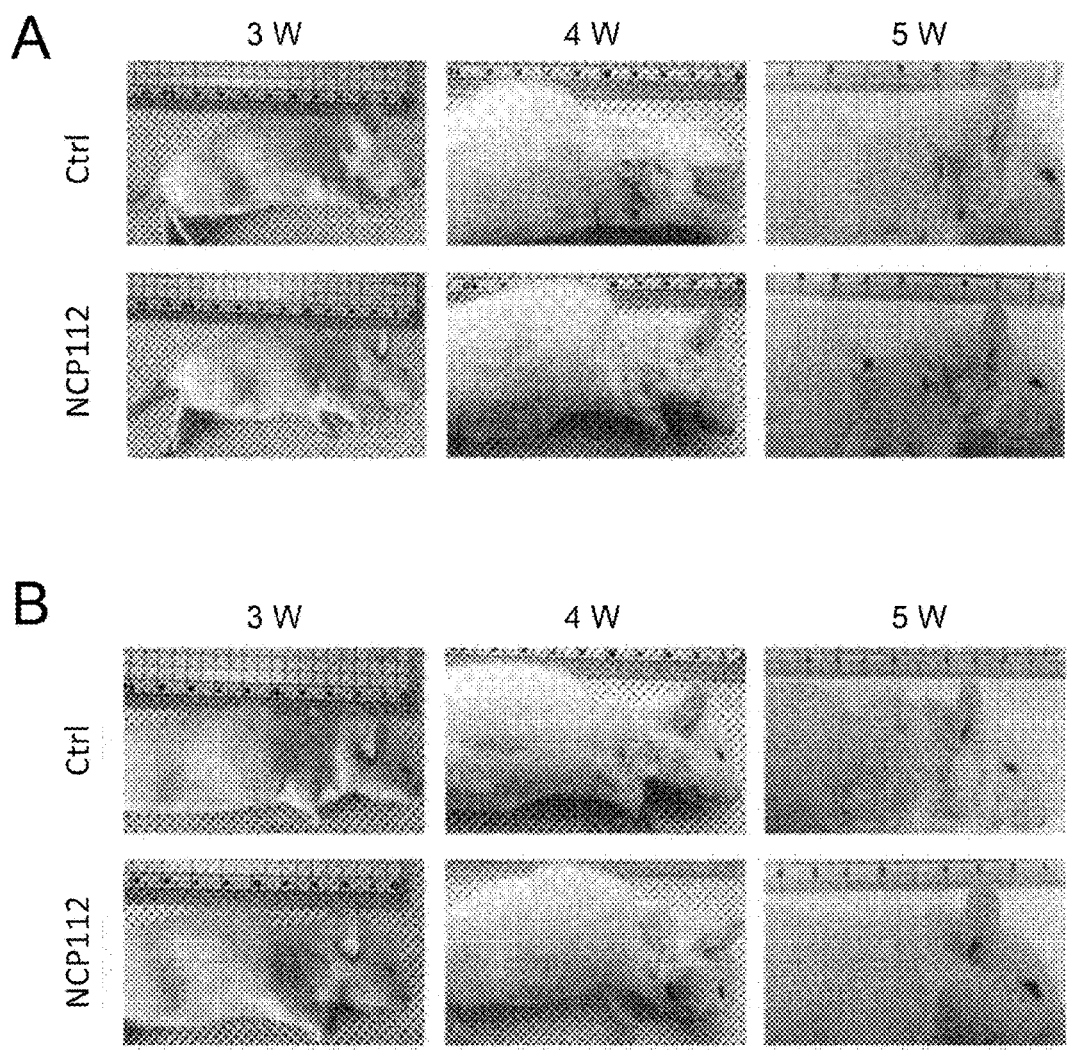
FIGS. 5A and 5B show a series of photographed images illustrating the results of skin conditions in a new model animal (Neo-Cap, A) and a 2-week-old model animal (2 W Cap, B), compared with those of the control group, according to time (3 to 5 weeks) after the peptide (NCP112) treatment according to an embodiment of the present invention.
Figure 6:
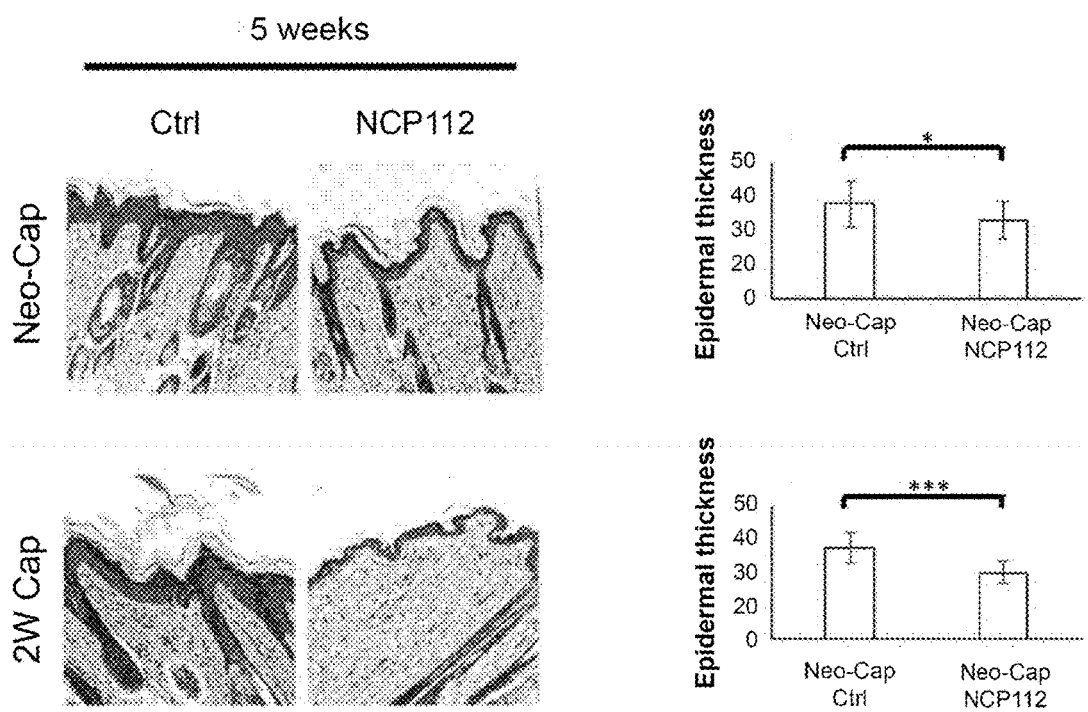
FIG. 6 shows the histological staining images (left panel) of skin tissue conditions observed under a microscope and the graphs (right panel) illustrating the measurement results with regard to epidermal thickness in a new model animal (Neo-Cap, top) and a 2-week-old model animal (2 W Cap, bottom) 5 weeks after the peptide (NCP112) treatment according to an embodiment of the present invention, respectively.

The mice analyzed in Experimental Example 3-1 were treated with the peptide according to an embodiment of the present invention, and after five weeks, the mice were sacrificed. The skin tissue at the site where dermatitis was induced by capsaicin treatment was removed in a size of about 3 cm×3 cm and the tissue was fixed in a 4% paraformaldehyde solution for two to three days. The fixed tissue was again fragmented into a size of 1 cm×0.5 cm and added into a cassette for tissue and underwent dehydration, transparency, and paraffinization using the tissue processor (Leica microsystems, Germany), and stored at −20° C. For the preparation of tissue section, paraffin blocks were cut into a size of 5 μm and the thinly cut tissue ribbons were floated in a constant-temperature water bath and flattened. The tissue sections were attached to a slide glass and dried on a heating plate at 40° C. To evaluate the pathological evaluation of skin tissue of the mice, the skin tissue sections were deparaffinized three times for 3 minutes with xylene, soaked in 70% to 100% ethanol for 1 minute, respectively, and finally washed with distilled water. After immersing the skin tissue sections in the hematoxylin solution, the nuclei of the tissue cells were stained, washed with distilled water, and then stained again with Eosin. The stained tissue was subjected to 70% to 100% ethanol and xylene in a reversed order of the deparaffinization process, and finally an embedding reagent was applied thereto and enclosed by covering with a cover glass. To observe under an optical microscope, stained tissue was photographed under 200× magnification and pathological evaluation was performed. FIG. 5 shows the images of the conditions of skin tissue in areas where atopic dermatitis was induced areas over time. FIG. 6 shows images illustrating the results of tissue staining for skin tissue at the site of atopic dermatitis, in which both Neo-Cap and 2 W Cap groups treated with the control group showed a thickening of the epidermis thus exhibiting the typical symptom of atopic dermatitis, whereas in the group treated with the peptide (NCP112) according to an embodiment of the present invention, a slight decrease of the epidermal layer in Neo-Cap group and a significant decrease in 2 W Cap group thus confirming the recovery close to the normal level. Accordingly, the results of animal experiment confirmed that the peptide according to an embodiment of the present invention exhibited an effect of ameliorating the symptom of atopic dermatitis in both Neo-Cap and 2 W Cap groups, and in particular, the animal model in 2 W Cap group exhibited skin conditions which were comparable to that of the normal conditions thus confirming the effectiveness of the peptide.

Although the present invention has been described with reference to the above-described Examples and Experimental Examples, they are provided herein for only illustrative purposes, and it will be understood by those skilled in the art that various modifications and equivalent other Examples and Experimental examples are possible without departing from the scope of the present invention. Accordingly, the true scope of the present invention should be determined by the technical idea of the appended claims.

INDUSTRIAL APPLICABILITY

The antimicrobial peptide according to an embodiment of the present invention not only exhibits an antibacterial activity against various bacteria such as gram-negative bacteria and gram-positive bacteria but also exhibits a distinguished effect of ameliorating symptoms of atopic dermatitis in an animal model of atopic dermatitis, thus being applicable as a raw material for functional cosmetics, etc. for ameliorating atopic dermatitis as well as various kinds of antibiotics, in particular, antibiotics for external skin agents.

Sequencing Listing Free Text

SEQ ID NO: 1 is an amino acid sequence of an antimicrobial peptide according to an embodiment of the present invention.

The invention claimed is:

1. An antibacterial and immune regulatory peptide consisting of the amino acid sequence of SEQ ID NO: 1.

2. The peptide of claim 1, wherein an octanoyl group ($CH_3(CH_2)_6CO$) is added to the N-terminus.

3. An antibacterial agent comprising the peptide of claim 1 as an active ingredient.

4. A pharmaceutical composition for treating atopic dermatitis, the pharmaceutical composition comprising the peptide of claim 1 as an active ingredient.

5. A cosmetic composition for ameliorating atopic dermatitis, the cosmetic composition comprising the peptide of claim 1 as an active ingredient.

6. An antibacterial agent comprising the peptide of claim 2 as an active ingredient.

7. A pharmaceutical composition for treating atopic dermatitis, the pharmaceutical composition comprising the peptide of claim 2 as an active ingredient.

8. A cosmetic composition for ameliorating atopic dermatitis, the cosmetic composition comprising the peptide of claim 2 as an active ingredient.

9. An antibacterial and immune regulatory peptide comprising the amino acid sequence of SEQ ID NO: 1, wherein one to six amino acids are added to the C-terminus of the amino acid sequence of SEQ ID NO: 1.

10. An antibacterial agent comprising the peptide of claim 9 as an active ingredient.

11. A pharmaceutical composition for treating atopic dermatitis, the pharmaceutical composition comprising the peptide of claim 9 as an active ingredient.

12. A cosmetic composition for ameliorating atopic dermatitis, the cosmetic composition comprising the peptide of claim 9 as an active ingredient.

13. The peptide of claim 9, wherein an octanoyl group ($CH_3(CH_2)_6CO-$) is added to the N-terminus.

14. An antibacterial agent comprising the peptide of claim 13 as an active ingredient.

15. A pharmaceutical composition for treating atopic dermatitis, the pharmaceutical composition comprising the peptide of claim 13 as an active ingredient.

16. A cosmetic composition for ameliorating atopic dermatitis, the cosmetic composition comprising the peptide of claim 13 as an active ingredient.

* * * * *